(12) United States Patent  (10) Patent No.: US 8,147,519 B2
Wilcox  (45) Date of Patent: Apr. 3, 2012

(54) VARIABLE ANGLE ROD CONNECTORS AND THE METHODS OF USE

(75) Inventor: Bryan Scott Wilcox, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1169 days.

(21) Appl. No.: 11/869,422

(22) Filed: Oct. 9, 2007

(65) Prior Publication Data

US 2009/0093847 A1  Apr. 9, 2009

(51) Int. Cl.
*A61B 17/70* (2006.01)
(52) U.S. Cl. .................................. 606/260; 606/259
(58) Field of Classification Search ............ 128/898; 606/250–253, 259–260, 279
See application file for complete search history.

(56) References Cited

U.S. PATENT DOCUMENTS

| | | | |
|---|---|---|---|
| 4,628,919 A | 12/1986 | Clyburn | |
| 5,122,140 A | 6/1992 | Asche et al. | |
| 5,643,263 A | 7/1997 | Simonson | |
| 5,693,053 A | 12/1997 | Estes | |
| 5,709,681 A | 1/1998 | Pennig | |
| 5,885,284 A * | 3/1999 | Errico et al. | 606/252 |
| 5,885,285 A | 3/1999 | Simonson | |
| 6,162,224 A | 12/2000 | Huebner | |
| 6,171,309 B1 | 1/2001 | Huebner | |
| 6,183,473 B1 | 2/2001 | Ashman | |
| 6,217,578 B1 | 4/2001 | Crozet et al. | |
| 6,471,703 B1 | 10/2002 | Ashman | |
| 6,537,275 B2 | 3/2003 | Venturini et al. | |
| 6,554,831 B1 | 4/2003 | Rivard et al. | |
| 6,554,832 B2 | 4/2003 | Shluzas | |
| 6,562,038 B1 | 5/2003 | Morrison | |
| 6,572,618 B1 | 6/2003 | Morrison | |
| 6,579,292 B2 | 6/2003 | Taylor | |
| 6,648,887 B2 | 11/2003 | Ashman | |
| 6,685,705 B1 | 2/2004 | Taylor | |
| 6,872,209 B2 | 3/2005 | Morrison | |
| 7,066,939 B2 | 6/2006 | Taylor | |
| 7,207,992 B2 | 4/2007 | Ritland | |
| 2002/0193794 A1 | 12/2002 | Taylor | |
| 2003/0191473 A1 | 10/2003 | Taylor | |
| 2005/0101954 A1 | 5/2005 | Simonson | |
| 2005/0228376 A1 | 10/2005 | Boomer et al. | |
| 2005/0228378 A1 | 10/2005 | Kalfas et al. | |
| 2006/0195088 A1* | 8/2006 | Sacher et al. | 606/61 |
| 2006/0229611 A1* | 10/2006 | Avery et al. | 606/61 |
| 2006/0271051 A1 | 11/2006 | Berrevoets et al. | |
| 2007/0112427 A1 | 5/2007 | Christy et al. | |

FOREIGN PATENT DOCUMENTS

WO   03037200 A2   5/2003
WO   WO 03/037200 A2 *  5/2003

* cited by examiner

*Primary Examiner* — Eduardo C Robert
*Assistant Examiner* — Julianna N. Harvey

(57) ABSTRACT

A spinal rod connector is disclosed that allows end-to-end connection of at least two spinal rods. The connector may allow for angular adjustment in the construct which is associated with the patient's anatomy. Percutaneous length adjustment of the spinal rods may be available with visual assessment of the length of the rods via viewing windows on the connector. A locking mechanism may be used to fix a determined angle of the connector dependent upon the anatomy of the patient. The angle may be adjusted if necessary during a subsequent procedure.

14 Claims, 6 Drawing Sheets

VARIABLE ANGLE ROD CONNECTORS AND THE METHODS OF USE

BACKGROUND

The present application relates generally to the field of spinal implant systems, and in particular, to a variable angle growth rod connector that may be implanted as part of a growth rod fusionless system.

The spine is subject to various pathologies that comprise its load bearing and support capabilities. Such pathologies of the spine include, for example, degenerative disease, the effect of tumors and, of course, fractures and dislocations attributable to physical trauma. In the treatment of diseases, malformations or injuries affecting spinal motion segments (which include two or more adjacent vertebrae and the disc tissue for disc space there-between), and especially those affecting disc tissue, it has long been known to remove some or all of a degenerated, ruptured or otherwise failing disc. It is also known that artificial disc, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment, in correcting abnormal curvatures and alignments of the spinal column, and for treatment of other conditions.

In spinal rod fixation procedures, bending the rod induces stress to the rod and decreases the fatigue strength of the material. In addition, the geometric and dimensional features of these rod systems and patient anatomy constrain the surgeon during surgery and prevent optimal placement and attachment along the spinal column. For example, elongated, one-piece rods can be difficult to bend and maneuver into position between the vertebral members along the spine which provides the surgeon with only limited options in sizing and selection of the rod system to be placed during surgery. A small child presents even more difficulties because of the growth patterns associated with the age of the child. Existing spinal implant systems and methods should accommodate for the various growth patterns as the child grows which can be typically handled by a growth rod fusionless system.

Thus, there is a need in the art for a growth rod fusionless system that can be used to accommodate the growth patterns and the various anatomies associated with the spine.

SUMMARY

The present application relates to connectors that may be implanted as part of a growth rod fusionless system. The connector may allow an angle to be set in the construct dependent on the patient's anatomy and where the connector is placed. The connector may also allow for a percutaneous length adjustment as the patient grows. A viewing feature in the connector may allow the surgeon to see how much rod is engaged in the connector to determine length adjustment capability.

In one embodiment, a spinal rod connector includes a first portion that may be adapted to receive a first spinal rod; a second portion that may be adapted to receive a second spinal rod; and a hinge portion that may connect the first and second portions end-to-end and allows an angle adjustment dependent upon the anatomy of the patient. The connector may allow the spinal rods to be joined end-to-end in a lengthwise orientation with both the capability to adjust and view the length of the rods. The hinge portion may include a locking mechanism that allows the first and second portions to be locked in the pre-determined angle and may allow for percutaneous angle adjustment.

In another embodiment, the hinge portion may include a hinge pin to allow angle adjustment and a locking fastener to lock the first and second portions in a pre-determined angle and may also allow for angle adjustment. Windows may be located in both the first and second portions to allow visual determinations of the length of rods that are needed for the construct.

In one embodiment, a system for connecting spinal rods in an end-to-end fashion includes first and second portions that are connected by a hinge pin. The system may allow end-to-end connection of two spinal rods whose lengths can be adjusted depending upon the anatomy of the patient.

Further features and advantages of the embodiments will become apparent to those skilled in the art in view of the detailed description of preferred embodiments which follows, when considered together with the attached drawings.

DETAILED DESCRIPTION

Figure 1:
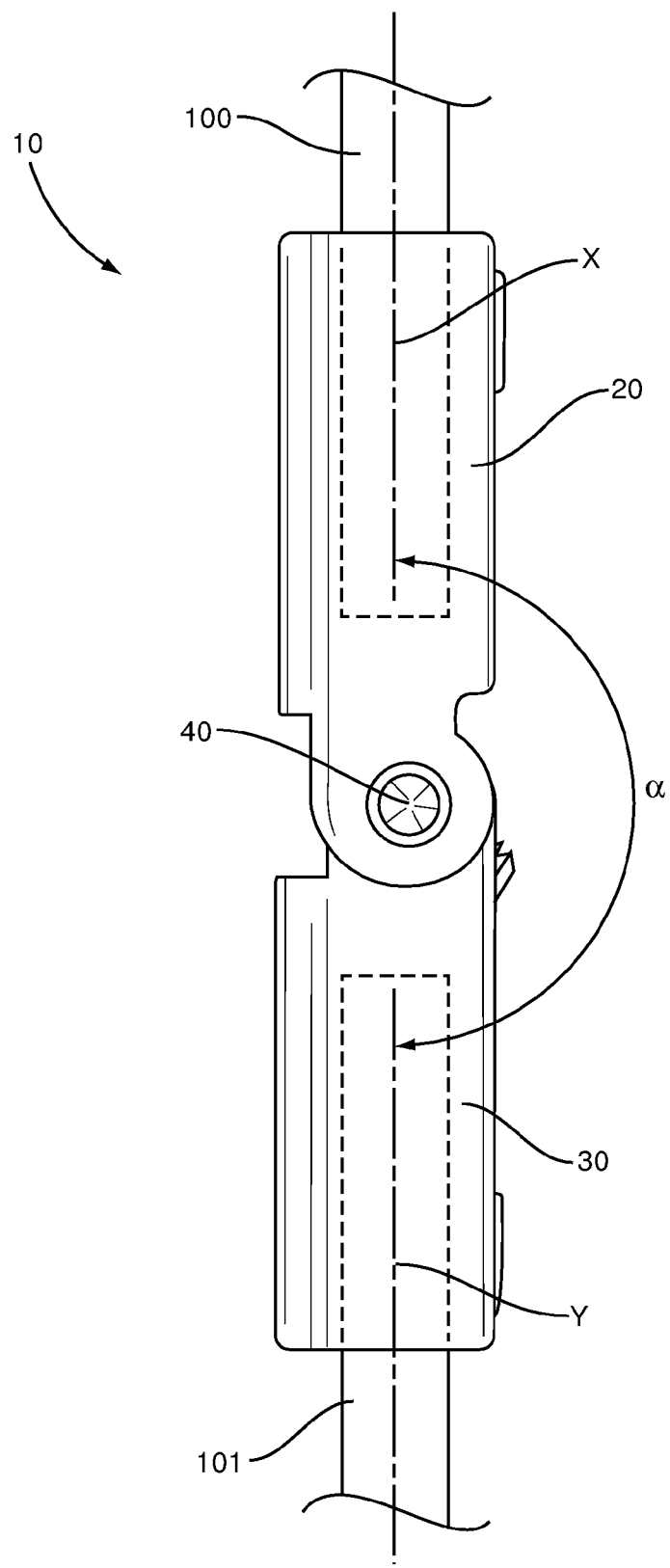
FIG. 1 is a schematic side view of a connector to connect first and second spinal rods according to one embodiment.

The present application is directed to a connector for connecting spinal rods. FIG. 1 illustrates a schematic view of one embodiment of the connector 10 that includes a first member 20 connected to a second member 30 with a hinge 40. The first member 20 is sized to receive a first spinal rod 100, and the second member 30 is sized to receive a second spinal rod 101. Hinge 40 provides for positioning the members 20, 30 and rods 100, 101 at a variety of angular orientations with centerlines X, Y of the rods 100, 101 forming an angle α. The angle α may vary for use in a first spinal application such as a lordotic section of the spine, and a second positioning for use in a second application such as a kyphotic section of the spine.

Figure 2:
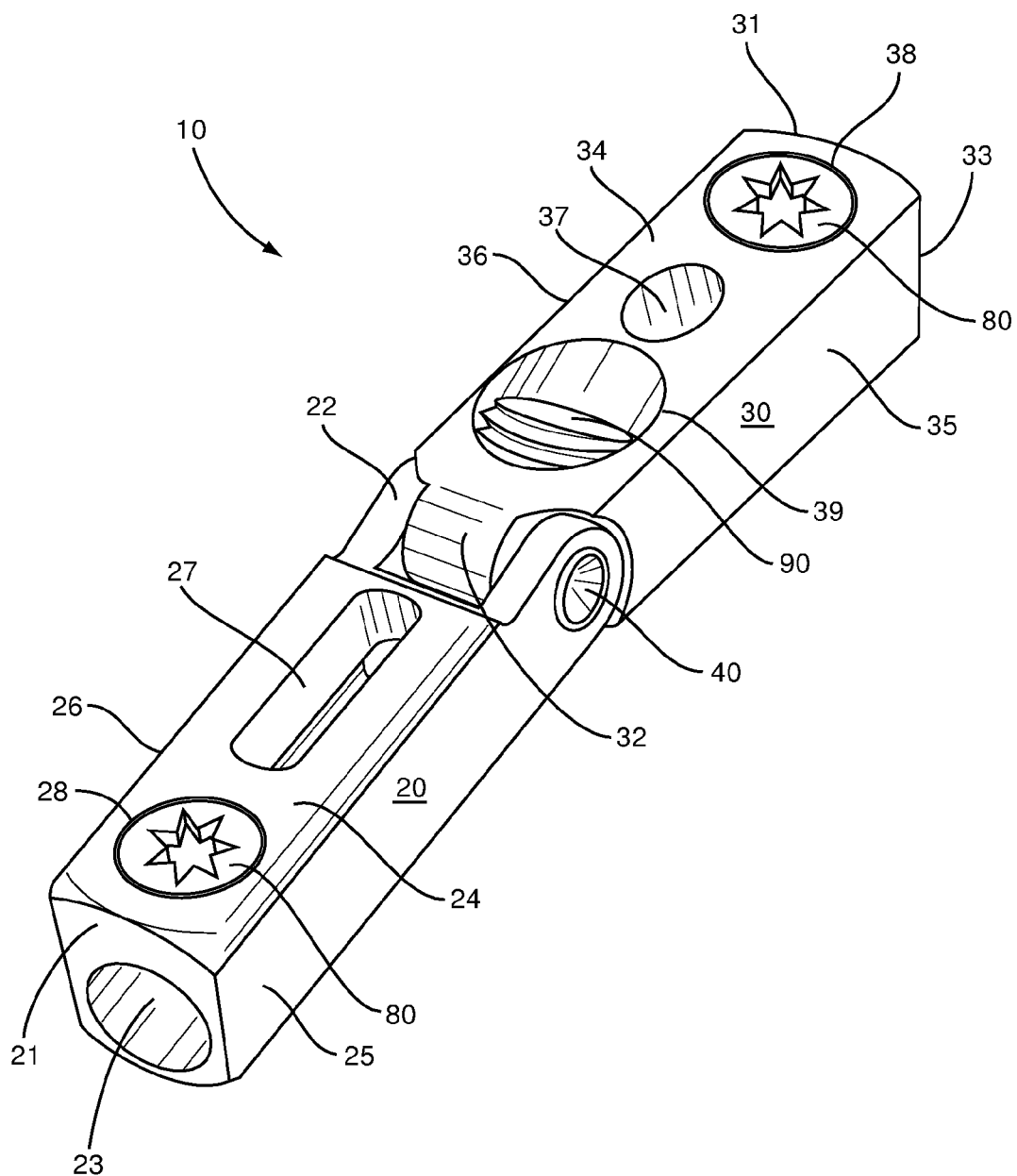
FIG. 2 is a perspective view of a connector according to one embodiment.

FIG. 2 illustrates one embodiment of the connector 10 comprising the first and second members 20, 30 connected by a hinge 40. First member 20 includes an elongated shape with a first end 21 opposite from the second end 22. A bore 23 extends inward from the first end 21 along a length of the first member 20. Bore 23 may include a variety of sectional shapes, including circular as illustrated in FIG. 2. The bore 23 may extend the entire length, or may terminate at a point in proximity to the second end 22. Bore 23 is positioned within an interior of the first member 20 and is enclosed by the sides of the member 20. In the embodiment of FIG. 2, first member 20 includes a first side 24 and opposing second and third sides 25, 26. The first side 24 is substantially flat, and is substantially perpendicular to the second and third sides 25, 26. In one embodiment, the first member 20 is cylindrical with the first side 24 being substantially flat.

A window 27 extends inward into the bore 23 from the first side 24. Window 27 provides for the physician to visual observe the positioning of the first rod 100 within the bore 23 as will be explained in detail below. Window 27 may include substantially smooth sidewalls. In the embodiment of FIG. 2, window 27 includes an elongated shape with a major axis and a minor axis. The major axis is substantially aligned with the bore 23.

An opening 28 also extends inward into the bore 23 from the first side 24. Opening 28 is threaded to receive a fastener 80 that connects the first member 20 to the first rod 100. In this embodiment, opening 28 is positioned between the window 27 and the first end 21.

The second member 30 shares many of the characteristics of the first member 20.

Second member 30 includes an elongated shape that extends between a first end 31 and a second end 32. A bore 33 is positioned within the second member 30 and extends inward from the first end 31 and may extend the entire length, or may terminate at a point inward from the second end 32. Bore 33 may include a variety of sectional shapes, including circular. Second member 30 includes a first side 34 and opposing second and third sides 35, 36. In this embodiment, the first side 34 is substantially flat and perpendicular to the second and third sides 35, 36. In one embodiment, the second member 30 is cylindrical with the first side 34 being substantially flat.

A window 37 extends inward into the bore 33 from the first side 34 for the physician to visually observe the positioning of the second rod 101 within the bore 33. Window 37 may include substantially smooth sidewalls. In the embodiment of FIG. 2, window 37 includes an elongated shape with a major axis and a minor axis. The major axis is substantially aligned with the bore 33.

An opening 38 also extends inward into the bore 33 from the first side 34. Opening 38 is threaded to receive a fastener 80 that connects the second member 30 to the first rod 101. In this embodiment, opening 38 is positioned between the window 37 and the first end 31.

Figure 3:
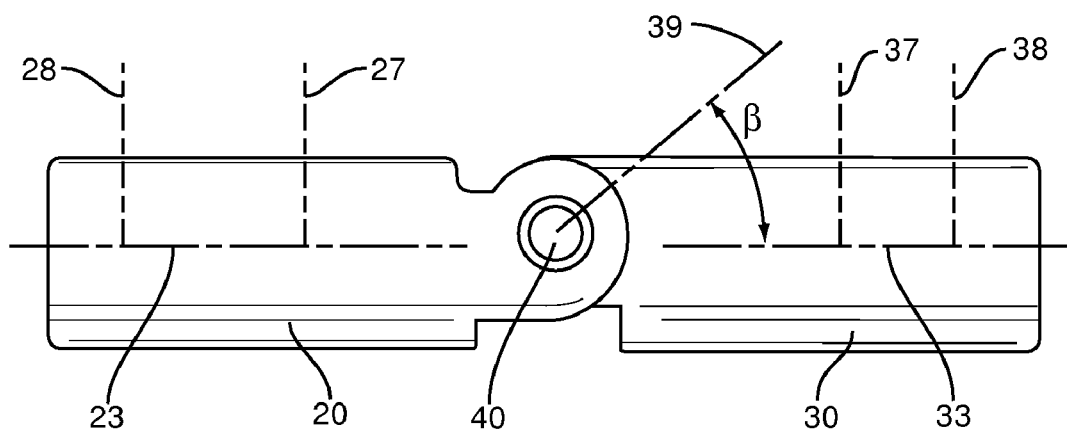
FIG. 3 is a schematic side view of a connector according to one embodiment.

A second opening 39 is positioned on the first side 34 and extends to the hinge 40. The second opening 39 is threaded to receive a fastener 90 that engages with the hinge 40 and locks the angular orientation of the first and second members 20, 30. As best illustrated in FIG. 3, opening 39 extends inward into the body 30 at an acute angle β relative to the bore 33. FIG. 3 also illustrates an embodiment with the window 27 and opening 28 being substantially perpendicular to bore 23 of the first member 20, and window 37 and opening 38 being substantially perpendicular to bore 33 of the second member 30.

Fasteners 80, 90 each include a body with exterior threads, a first end with a tool-receiving receptacle, and a second end with a contact surface. Contact surfaces on the fasteners 80 are configured to contact and engage with the spinal rods 100, 101. Fastener 90 includes a contact surface that contacts and engages with the hinge 40. Each of the fasteners 80, 90 may be substantially the same, or each may be different. In one embodiment, the contact surface 90 on the fastener includes splines that engage with splines that extend from the hinge 40.

Hinge 40 extends through each of the first and second members 20, 30. In one embodiment, hinge 40 is fixedly attached to the first member 20, and movably attached to the second member 30. In this manner, second member 30 may move relative to the first member 20 and hinge 40 prior to securing the positioning with the fastener 90.

Figure 4:
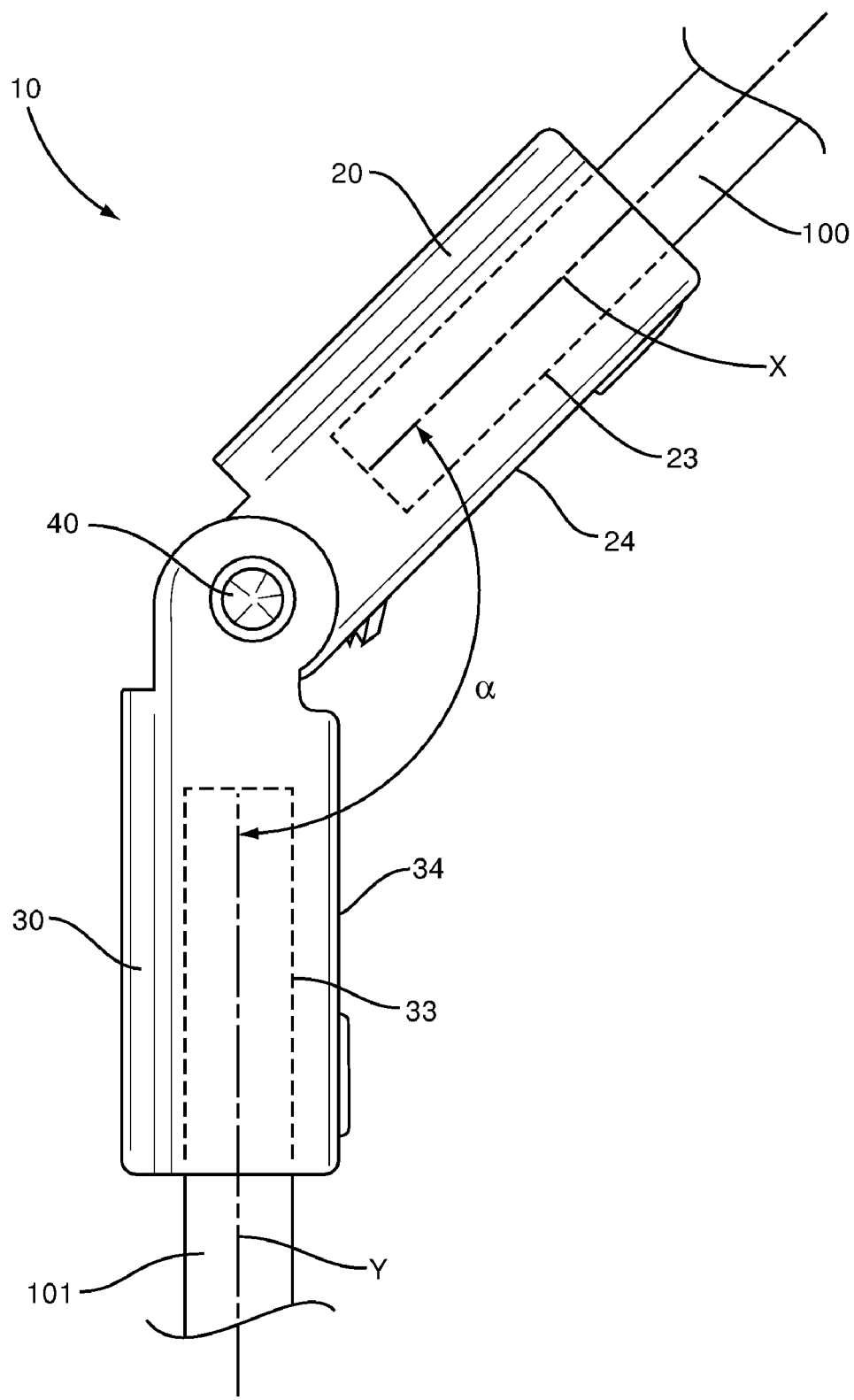
FIG. 4 is a side view of a connector in an angular orientation according to one embodiment.
Figure 5:
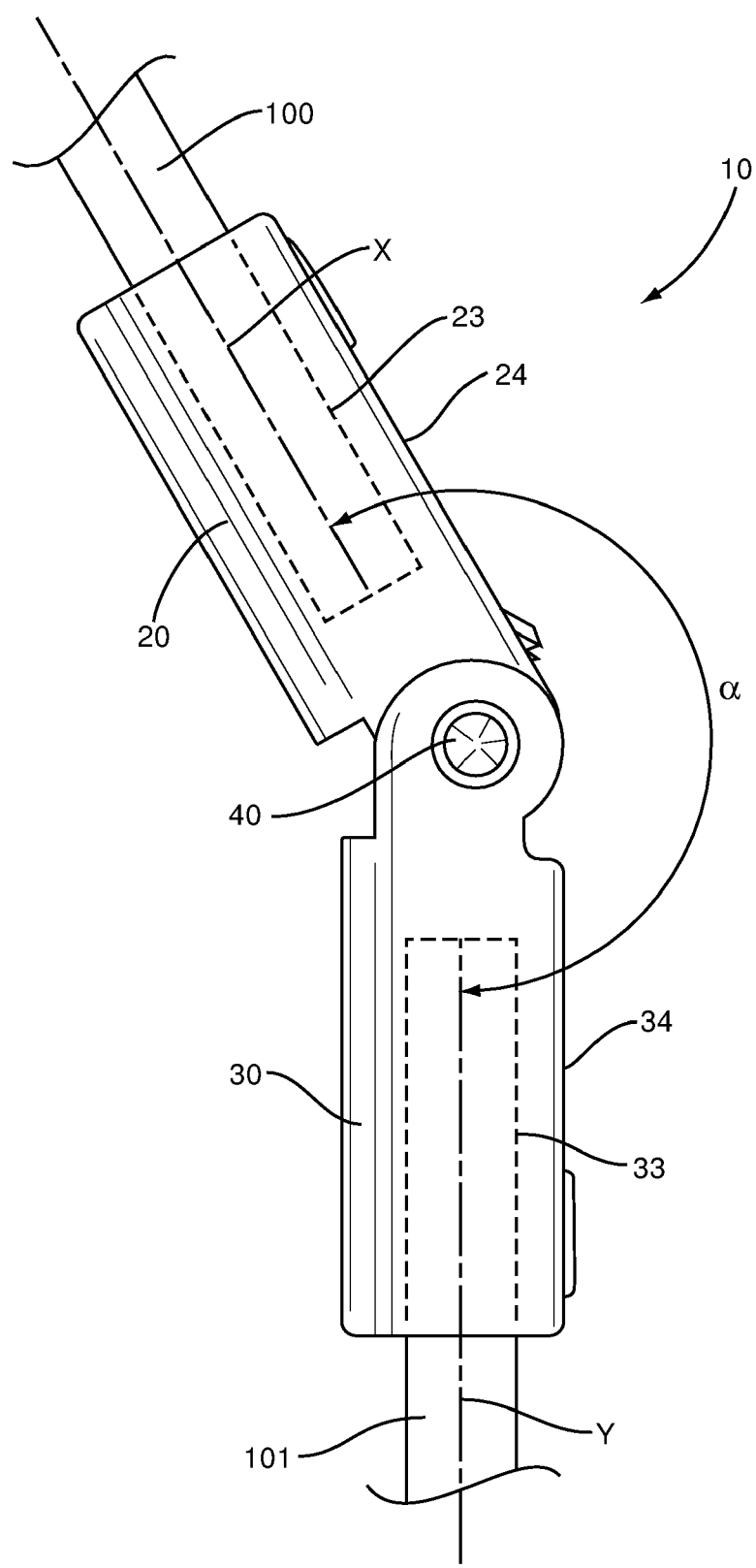
FIG. 5 is a side view of a connector in an angular orientation according to one embodiment.

The hinge 40 provides for selectively positioning the angle formed between the first and second members 20, 30. FIG. 4 illustrates the first rod 100 positioned within the bore 23 of the first member 20, and the second rod 101 positioned within the bore 33 of the second member 30. The first and second members 20, 30 are positioned at an angular position about the hinge 40 to form an angle α formed between the centerlines X, Y of the rods 100, 101. FIG. 5 illustrates the connector 10 in a second orientation with the first and second members 20, 30 being relatively moved to increase the angle α. The connector 10 may be used in a variety of different contexts because of the ability to vary the angle α between an angle such as illustrated in FIG. 4 and larger angle in FIG. 5. The connector 10 may be used in a first context as illustrated in FIG. 4, such as with a lordotic section of the spine. The same connector 10 may be adjusted and used in a second context as illustrated in FIG. 5, such as a kyphotic section of the spine. Further, the angle α may be adjusted to accommodate the various spinal locations of the connector 10. In one embodiment, the angle α may range from between about 60° to about 120°.

Figure 6:
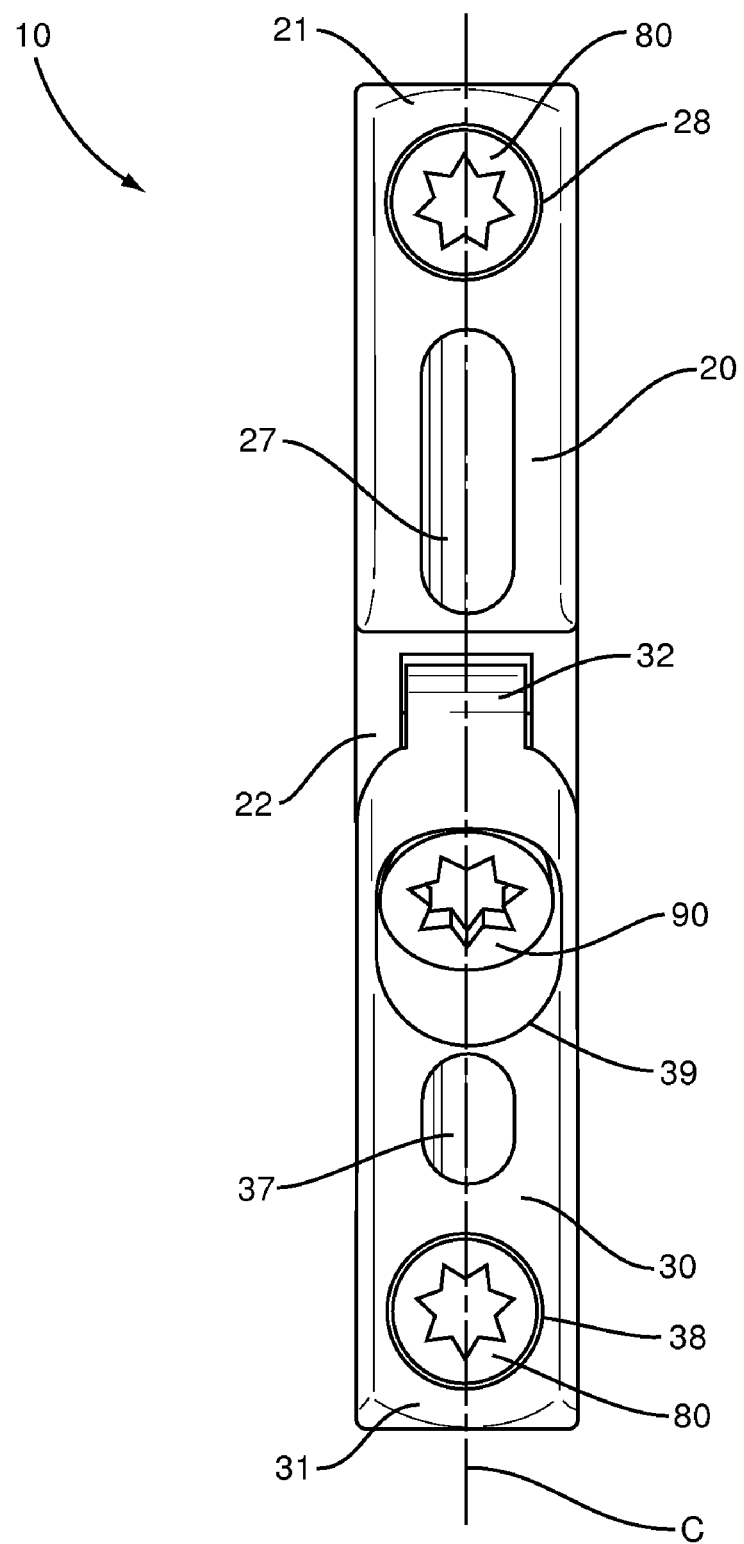
FIG. 6 is a top view of a connector according to one embodiment.

FIG. 6 illustrates one embodiment of a top view of the connector 10. A centerline C extends through each of the first and second members 20, 30 and aligns with the bores 23, 33. Each of the windows 27, 37, and openings 28, 38, 39 are substantially centered along the centerline C. The bores 23, 33 are positioned to orient the rods 100, 101 within a common plane, and in an end-to-end orientation. A physician is able to access each of the windows 27, 37 and openings 28, 38, 39 from a single direction to facilitate adjustment of the connector 10. In one embodiment, connector 10 is positioned within the patient such that the windows 27, 37 and openings 28, 38, 39 face outward. This positioning provides for the windows and openings to be accessed in a minimally invasive manner with only minor incisions in the patient necessary to access the connector 10. In one embodiment, this positioning provides for the openings 28, 38, 39 to be accessed in a percutaneous procedure.

In one method of use, the first rod 100 is inserted within the first bore 23 of the first member 20. The interior surface of the first bore 23 may be substantially smooth to facilitate insertion of the rod 100. During insertion, the physician is able to look through the window 22 and visually observe the location of the rod 100 within the bore 23. Once the rod 100 is axially positioned within the bore 23, the fastener 80 within the opening 28 is tightened to contact the rod 100 and secure the axial location within the bore 23. In a similar fashion, rod 101 is inserted into the second bore 33. Again, the physician may be able to visually observe the axial movement of the rod 101 within the bore 33 through the window 37. Once axially positioned, fastener 80 is tightened to within the opening 38 to contact and secure the rod 101.

Once the rods 100, 101 are secured, the members 20, 30 are moved about the hinge 40 to the desired angle α. Once set, fastener 90 is tightened within the opening 39 to contact the hinge and secure the relative positions of the members 20, 30. The connector 10 may be positioned relative to the vertebral members such that the first sides 24, 34 face in a direction that may be accessed in a subsequent, revision surgical procedure. The order of attachment of the rods 100, 101, and securing the members 20, 30 at the desired angle α may vary. By way of example, the angle α may be set prior to attaching one or both rods 100, 101 within the members 20, 30.

In some instances, a revision procedure is necessary to adjust the positions of one or both rods 100, 101, and/or change the angle α. The revision procedure may be performed in a minimally-invasive manner because of the positioning of the fasteners 80, 90. In one embodiment, the procedure is percutaneous with a small incision is made into the patient to access the fasteners 80, 90. A tool is inserted into the incision to loosen the fasteners 80 and adjust the axial position of the rods 100, 101 as necessary. The physician may be able to view the position of the rods through the windows 27, 37. Once positioned, fasteners 80 are tightened to contact the rods 100, 101 and lock the position. Likewise, a tool is inserted into the incision to loosen the fastener 90 and adjust the angular position if necessary. Once adjusted, fastener 90 is tightened to lock the angular position.

FIGS. 2 and 6 illustrate one embodiment with the first member 20 including a large window 27, and second member 30 including a smaller window 37. The size of the windows may vary depending upon the context of use and need for the physician to observe the position of the rods 100, 101. In one embodiment, the windows 27, 37 are substantially identical.

In one embodiment, the cross-sectional shape of the bores 23, 33 are substantially circular. In other embodiment, the cross-sectional shape may vary such as but not limited to rectangular, polygonal, oval, and triangular. The bores 23, 33 may include the same shape and size, or may include different shapes and/or sizes.

One embodiment of a spinal rod connector is disclosed in U.S. patent application Ser. No. 11/093,487 herein incorporated by reference in its entirety.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A device to connect first and second spinal rods comprising:
   a connector including first and second members pivotally connected together at an intermediate hinge, the first member including a first longitudinal bore to receive the first spinal rod and the second member including a second longitudinal bore to receive the second spinal rod, the first and second longitudinal bores being positioned to position the first and second spinal rods in an end-to-end orientation;
   the first member including a first opening to receive a first fastener to secure the first spinal rod within the first longitudinal bore, and a first window with a major axis that aligns with the first longitudinal bore to visually observe the first spinal rod in the first longitudinal bore, each of the first opening and the first window extending into the first longitudinal bore;
   the second member including a second opening to receive a second fastener to secure the second spinal rod within the second longitudinal bore, and a second window with a major axis that aligns with the second longitudinal bore to visually observe the second spinal rod in the second longitudinal bore, each of the second opening and the second window extending into the second longitudinal bore;
   the second member further including a third opening to receive a third fastener that engages with the hinge to lock an angular position of the first and second members;
   the second window being spaced away and separate from the second opening and being disposed directly between the second opening and the third opening,
   wherein the third opening extends into the second member at an acute angle relative to the second longitudinal bore.

2. The device of claim 1, wherein the first and second windows have interior sides which are substantially smooth.

3. The device of claim 1, wherein one of the first and second windows includes an elongated shape with a major axis and a minor axis, the major axis being substantially parallel with one of the longitudinal bores.

4. The device of claim 1, wherein the first opening is located a greater distance from the hinge than the first window, and the second opening is located a greater distance from the hinge than the second window.

5. The device of claim 1, further including a locking member that extends into one of the first and second members and contacts the hinge to selectively lock the first and second members at a desired angular orientation.

6. The device of claim 1, wherein each of the first, second, and third openings, and the first and second windows extend into a first side of the connector.

7. The device of claim 1, wherein the hinge is a pin that extends through the first and second members, the pin being fixedly connected to the first member to prevent relative movement between the first member and the pin, the pin being movably connected to the second member to allow relative movement between the second member and the pin.

8. A device to connect first and second spinal rods comprising:
   a connector including first and second members pivotally connected together at an intermediate hinge, the first member including a first longitudinal bore to receive the first spinal rod and the second member including a second longitudinal bore to receive the second spinal rod, the first and second longitudinal bores being positioned to position the first and second spinal rods in an end-to-end orientation;
   the first member including a first opening to receive a first fastener to secure the first spinal rod within the first longitudinal bore, and a first window with a major axis that aligns with the first longitudinal bore to visually observe the first spinal rod in the first longitudinal bore, each of the first opening and the first window extending into the first longitudinal bore;
   the second member including a second opening to receive a second fastener to secure the second spinal rod within the second longitudinal bore, and a second window with a major axis that aligns with the second longitudinal bore to visually observe the second spinal rod in the second longitudinal bore, each of the second opening and the second window extending into the second longitudinal bore;
   the second member further including a third opening to receive a third fastener that engages with the hinge to lock an angular position of the first and second members;

the second window being spaced away and separate from the second opening and being disposed directly between the second opening and the third opening, wherein each of the first, second, and third openings, and the first and second windows extend into a first side of the connector.

9. The device of claim 8, wherein the hinge is a pin that extends through the first and second members, the pin being fixedly connected to the first member to prevent relative movement between the first member and the pin, the pin being movably connected to the second member to allow relative movement between the second member and the pin.

10. The device of claim 8, wherein the first and second windows have interior sides which are substantially smooth.

11. The device of claim 8, wherein one of the first and second windows includes an elongated shape with a major axis and a minor axis, the major axis being substantially parallel with one of the longitudinal bores.

12. The device of claim 8, wherein the first opening is located a greater distance from the hinge than the first window, and the second opening is located a greater distance from the hinge than the second window.

13. The device of claim 8, further including a locking member that extends into one of the first and second members and contacts the hinge to selectively lock the first and second members at a desired angular orientation.

14. The device of claim 13, wherein the third opening extends into the second member at an acute angle relative to the second longitudinal bore.

* * * * *